United States Patent [19]

Ozyagcilar

[11] 4,139,551

[45] Feb. 13, 1979

[54] CATALYST FOR METHANE AND ETHANE SYNTHESIS

[75] Inventor: Mehmet N. Ozyagcilar, Columbia, S.C.

[73] Assignee: The Rafel Industrial Group, Ltd., Hamilton, Bermuda

[21] Appl. No.: 797,294

[22] Filed: May 16, 1977

Related U.S. Application Data

[63] Continuation-in-part of Ser. No. 772,360, Feb. 14, 1977, abandoned.

[51] Int. Cl.$^2$ .......................... C07C 1/02; C07C 1/04; C07C 1/12
[52] U.S. Cl. ...................... 260/449.6 R; 210/449.6 M; 252/472
[58] Field of Search .................. 260/449 M, 449.6 R, 260/449.6 M, 449 R; 252/472

[56] References Cited

U.S. PATENT DOCUMENTS

| | | | |
|---|---|---|---|
| 2,183,145 | 12/1939 | Michael et al. | 260/449.6 |
| 2,543,327 | 2/1951 | McGrath et al. | 252/472 |
| 2,593,250 | 4/1952 | Black et al. | 260/449.6 |
| 2,683,726 | 7/1954 | McGrath et al. | 260/449.6 |
| 2,781,325 | 2/1957 | Rottig et al. | 252/472 |
| 3,382,106 | 5/1968 | Jung et al. | 423/645 |
| 3,776,855 | 12/1973 | Raymond et al. | 423/645 |
| 3,967,936 | 7/1976 | Tajbl et al. | 260/449 M |

OTHER PUBLICATIONS

Reilly et al., Inorg. Chem., vol. 13, No. 1, 1974, 218-222.

*Primary Examiner*—Howard T. Mars
*Attorney, Agent, or Firm*—Townsend M. Belser, Jr.

[57] ABSTRACT

Bimetallic alloys of iron and titanium are employed as catalysts for combining hydrogen and the oxides of carbon to yield methane, ethane and other hydrocarbons and alcohols. The alloy composition is first activated by treatment with hydrogen gas at elevated temperatures and pressures. Particle size is also reduced by hydriding and dehydriding one or more times.

15 Claims, No Drawings

CATALYST FOR METHANE AND ETHANE SYNTHESIS

BACKGROUND

This is a continuation-in-part of Application Ser. No. 772,360 filed on Feb. 14, 1977 and subsequently abandoned in favor of this broader disclosure.

This invention relates to the synthesis of methane, ethane and other hydrocarbons and alcohols from hydrogen and the oxides of carbon through the use of a new catalyst and novel processes based thereon. These catalytic processes can also be used for the removal of carbon oxides from process streams where their presence is undesirable. Furthermore, the oxides of carbon can be hydrogenated to produce even higher hydrocarbons and various alcohols.

Prior art methods for the production of methane and ethane have employed carbon monoxide and hydrogen over nickel catalysts of various types. The cost of nickel catalysts is quite high, because of both raw material costs and difficulties experienced in the manufacturing process, the latter requiring that the nickel be supported on some type of inert base. Furthermore, the attrition of nickel catalysts is high because the reaction requires relatively high temperatures, which in turn causes a sintering type of breakdown that rapidly decreases the activity of the catalyst with time.

Nickel catalysts are also sensitive to poisoning by a number of the impurities usually found in hydrogen and carbon oxide reactants. Hydrogen sulfide has been found to poison nickel catalysts, even in very small concentrations, by forming nickel sulfide. The thermodynamics of the system is such that sulphur poisoning can be reversed by raising the temperature or increasing the hydrogen to hydrogen sulfide ratio in the feed or both. However, the use of higher operating temperatures with nickel catalysts are restricted by sintering problems. Also, the purity of the feed gas has inherent limitations dictated by the costs of purification.

As previously indicated, one of the present raw materials for methane production is carbon monoxide. This gas is most often produced by gasification of coal at relatively high temperatures of 500° C. or better. Carbon monoxide is also produced from hydrogen and carbon dioxide by conventional water-gas shift reactions which require even higher temperatures above 500° C. The reaction of carbon monoxide with hydrogen in the presence of nickel catalysts also requires similarly elevated temperatures in the range of 300° to 500° C. to produce significant reaction rates. These ranges of temperatures cause relatively rapid deterioration of the nickel catalysts. In addition, very little ethane can be produced with nickel catalysts since the ethane reaction is favored only at lower temperatures. Furthermore, practically no alcohol formation is observed over nickel catalysts. In general, the formation of alcohols is thought to follow a mechanism different from that prevailing in the synthesis of hydrocarbons. Heretofore, a different catalyst, namely zinc oxide, was required for the synthesis of methanol.

A further problem restricting the use of prior art catalysts is carbonyl formation. The carbonyls of metals like nickel, ruthenium and iron are extremely toxic compounds. They also have very low boiling temperatures such that they would be present in their vapor states at the usual temperatures for synthesis of methane, ethane and the higher carbon compounds. Carbonyl formation thus causes depletion of the catalyst as well as posing severe health and safety problems. Such problems with prior art catalysts can be avoided only by carefully controlling the operating temperature, pressure, the carbon oxide to hydrogen ratio, and other operating parameters and conditions.

Even at the elevated temperatures indicated, the reaction rates with nickel and other known catalysts are relatively slow and require a high residence time in the reactor vessel, which in turn produces a relatively slow production rate for the final product desired. At the present time, the production rate by known processes using carbon monoxide is marginally economical from the standpoint of the value of the final product which must compete with natural gas of comparable value. Since known reactions of carbon dioxide with hydrogen over prior catalysts require even higher temperatures and proceed at slower reaction rates as compared to corresponding reactions with carbon monoxide, the use of carbon dioxide as a feed material for methane production has not proven economically feasible to date. Furthermore, reactions with carbon dioxide have heretofore failed to produce any significant quantities of ethane or higher hydrocarbons which are more valuable as fuel because of higher heat values.

SUMMARY OF INVENTION

The foregoing disadvantages encountered with the carbon monoxide-hydrogen reaction over nickel catalysts are avoided through the use of the present invention. The present invention for the first time allows the use of carbon dioxide for the production of methane on a commercial basis. The mixture of carbon dioxide and hydrogen is passed over a novel catalyst formed of a hydrided binary alloy of iron and titanium. The catalysts described also greatly enhance the reactions for synthesis of methane, ethane and higher hydrocarbons and alcohols from carbon monoxide and hydrogen. As might be expected, reaction rates are faster with a carbon monoxide feed as compared to those attainable with the carbon dioxide feed, and this reaction also gives greater yields of ethane, alcohols and the more complex carbon compounds relative to the methane yield.

The reaction rate obtainable at a given temperature with this new process is greater by a factor of at least 2 than that experienced with prior art catalysts and reactions. Furthermore, there is no attrition of the type causing deterioration of nickel catalysts. To the contrary, the activity of the Fe-Ti catalyst increases with aging in the hydrogen atmosphere which cracks the catalyst particles both microscopically (surface cracks) and macroscopically (into smaller particles), with attendant increases in active surface area. There is also much less poisoning or deactivation of the catalyst through smothering of the adsorbing sites with the reactants themselves. By controlling process conditions, activation of this new catalyst can continue simultaneously with the production reaction.

The unit cost of the new catalyst is also substantially less than that of prior art catalysts, the cost of the raw materials as well as the cost of actually producing the catalyst being less. In this regard, the Fe-Ti catalyst is used in its unsupported form, resulting in substantial cost savings in making up the catalyst bed.

It is also possible with the new catalyst to attain significant reaction rates at substantially lower temperatures than those previously employed in the prior art for methane and ethane synthesis. These lower temperatures are particularly favorable for the formation of ethane and lesser amounts of higher hydrocarbons and alcohols which are more valuable as a fuel than methane because of their higher heat values.

It also follows that greater reaction rates at a given temperature are obtainable by a relatively small increase in pressure. Operating temperatures as low as 150° C. at pressures as low as 30 atmospheres are believed to be possible in commercial processes based on the new catalyst.

With regard to the cost of raw materials, carbon dioxide is significantly cheaper than carbon monoxide and is much safer to use. With reference specifically to coal gasification as the source of feed materials, lower temperatures favor the formation of carbon dioxide over the formation of carbon monoxide, resulting in a substantial energy saving in providing those raw materials for subsequent methane and ethane synthesis. With regard to safety, it is well known that carbon monoxide is an extremely hazardous material while there is no such disadvantage in employing carbon dioxide as the carbon oxide component of the feed material. Of course, the overall economics of the specific production processes and equipment employed will dictate whether to use carbon monoxide, carbon dioxide, or a mixture of both, in the feed stream.

It is therefore an object of this invention to provide a novel process for the manufacture of methane and ethane from carbon dioxide and hydrogen.

Another object of the present invention is the manufacture of methane and ethane using less expensive raw materials and a less expensive catalyst than heretofore employed.

Yet another object of the present invention is to provide a process for making methane and ethane at substantially increased production rates from raw materials produced by gasification or coking of coal.

A further object of the present invention is to provide a commercial process for the production of methane and ethane at lower temperatures and pressures than previously possible.

Still another object of the present invention is to employ in the production of methane and ethane a long-lived catalyst capable of being continuously activated during the production process.

A further object of the present invention is to produce a catalyst resistant to any loss of activity at the reaction temperatures required for the production of methane and ethane from carbon oxides and hydrogen and resistant to poisoning by contaminants found in commercial grades of carbon oxides and hydrogen.

A still further object of the invention is to provide a novel catalyst for the production of methane and ethane which does not contain any constituents for the formation of a carbonyl compound from the carbon oxides present.

Another object of the present invention is to provide a catalytic process for the removal of carbon oxides from gaseous process streams where their presence is undesirable.

A further object of the present invention is to economically increase the heating value of the gas initially obtained from coal gasification by converting the carbon dioxide, carbon monoxide, and hydrogen components of that gas to methane, ethane and higher hydrocarbons by catalytic synthesis.

Another object of the invention is to provide a commercially feasible process for the production of a gasoline fuel substitute by converting hydrogen and the oxides of carbon into a methane-ethane mixture also containing alcohols and other liquid hydrocarbons.

The exact nature of the invention as well as other objects and advantages thereof will be readily apparent from the following specific description of the preferred embodiment of the invention.

DETAILED DESCRIPTION

The catalyst of the present invention is comprised of a binary or bi-metallic alloy of iron and titanium with compositions in the range from 2 moles of iron per mole of titanium to 1 mole of iron to 3 moles of titanium. It has been found that when hydrided these alloy compositions form extremely active catalysts for the production of methane and ethane, along with smaller amounts of corresponding alcohols and higher hydrocarbons, from hydrogen and the gaseous oxides of carbon principally carbon dioxide and carbon monoxide. The specific alloys used are available from the International Nickel Company. These alloys are described in a book entitled *Constitution of Binary Alloys, First Supplement* as authored by R. P. Elliott and published by McGraw-Hill, New York, N.Y., 1965, and also in the paper of Reilly, et al. referenced fully below. They are formed from the relatively pure metals by a melting process at temperatures in the range of 1500° to 1900° C. The alloy compositions found active as catalysts here always contain as one of the alloy phases the bimetallic compound having a titanium to iron ratio of 1.0. The catalysts are preferably made from commercial grade titanium and electrolytic iron. The alloy composition with a titanium to iron mole ratio of 1 to 2 is also an intermetallic compound. Alloys with a titanium to iron ratio of greater than 1 consist of two phases, three such alloys being those with a titanium to iron ratio of 1.1, 2 and 3. These latter are more active. The preferred bi-metallic alloy used as a catalyst in this invention is that having a composition of 1.1 moles of titanium to 1 mole of iron.

It is to be understood that all alloy compositions containing the 1 to 1 binary compound of these two metals are catalytically active for methane and ethane formation. Compositions with mole ratios of titanium to iron in the range of 0.5 to 3.0 have been actually tested and are preferred. Compositions richer in titanium do not appear to be commercially available due to difficulties experienced in their manufacture. The catalysts are active at all temperatures at and above room temperature (20° C.) and at all pressures at and above atmospheric, the higher the temperature and the pressure, the greater the rate of reaction. The activity of the catalysts were found to be in the following order from highest activity to least activity: titanium to iron ratio of 1.1, titanium to iron ratio of 2.0, titanium to iron ratio of 3.0, titanium to iron ratio of 1.0, and titanium to iron ratio of 0.5. Therefore the preferred catalyst for this reaction is that of highest activity, namely, the titanium to iron ratio of 1.1. It follows that the catalyst with a titanium to iron ratio of 2 is the second most active. It is believed that both the hydride form of the alloy (Iron Titanium Hydride) and the Fe-Ti alloy itself are catalytically active in the reactions concerned.

Prior to using the binary alloy as a catalyst, it is activated with hydrogen, first to remove oxides and other impurities and then to produce iron titanium hydrides. When the alloy is received from the manufacturer, it is relatively large in size (larger than 16 mesh) and is coated with an oxide layer. In this form, the bi-metallic alloy will not form the hydrides which are believed to be one of the active forms of the catalyst. Activation of the catalyst also removes other surface impurities such as carbon and nitrogen compounds.

Activation of the catalyst is accomplished by treating it with hydrogen at temperatures in the range of 200° to 400° C. and a pressure of approximately 200 psia. The catalyst is further activated by successively outgassing and treating it with pressurized hydrogen so that it is alternately dehydrided and hydrided. This second step of the activation process causes multiple cracks in the surface of each particle and breaks up the catalyst particles into smaller particles, thereby greatly increasing the reactive surface area of the bed. This process preferrably is continued until the average particle size is approximately 200 mesh. The hydriding cycle is generally carried out at room temperature and 1,000 psia and the dehydriding cycle at approximately 200° C. with outgassing. Outgassing may be accomplished at atmospheric pressure with helium purging or by drawing a slight vacuum of one or two inches of water.

Following the activation steps, a gaseous feed stream comprised of carbon oxides and hydrogen is continually passed over the catalyst bed in the production reaction that gives a high yield of methane and ethane in the product, with methane being the greater component by a ratio of at least 10 to 1. Although significant yields of the product are obtainable at room temperature (20° C.) and atmospheric pressure, commercial yields require higher temperatures and pressures in the range of 100° to 200° C. and 30 to 200 atmospheres of pressure. Greater temperatures and pressures will yield even greater reaction rates which are limited only be restrictions on equipment parameters and adverse side reactions such as smothering the catalyst with deposited carbon from either the breakdown of carbon dioxide or the cracking of methane or ethane. At temperatures at or above 200° C. and pressures at or above 100 atmospheres yields approaching 100% of theoretical are attainable.

Catalytic activity appears to be the optimum when the partial pressure of the hydrogen used in hydriding is equal to or greater than the equilibrium dissociation pressure of iron titanium hydride. It is therefore believed, as previously indicated, that the most active state of the catalyst is the hydride form of the alloy, without any intention of being bound by this hypothesis. The partial pressure of the hydrogen to be used at a given temperature to achieve the optimum reaction rate can therefore be determined from the equilibrium dissociation pressure of iron titanium hydride at that temperature, the latter relationship being set forth in the literature. For determination of this pressure, particular reference is made to the article entitled "Formation and Properties of Iron Titanium Hydride" by J. J. Reilly and R. H. Wiswall, Jr., of Brookhaven National Laboratory as published in *Inorganic Chemistry*, Volume 13, No. 1, 1974, at pages 218 through 222.

The preferred processes for both activating the catalyst and subsequently producing methane and ethane through the use thereof with a carbon dioxide feed are set out below.

The catalyst as purchased is charged to a conventional reactor vessel such as presently used in producing methane from carbon monoxide and hydrogen. The reactor is heated to 400° C. and purged with helium for approximately six to eight hours. While maintaining the vessel at 400° C., the reactor is pressurized with hydrogen to 200 psia and maintained in that condition for approximately three to four hours. This step is sufficient to remove the oxide films and other adsorbed impurities from the surface of the catalyst so as to enhance diffusion of hydrogen into the alloy, as well as later adsorption of the reactant gases during the production reaction. The initial treatment of the catalyst with hydrogen is preferably carried out with the hydrogen confined to the reactor vessel in a static condition, instead of utilizing any type of flow regime.

The reactor is then allowed to cool to room temperature (20° to 25° C.) and throughout the cooling process is continuously purged with helium to outgas the hydrogen. Upon reaching room temperature, the reactor is pressurized with hydrogen to 1,000 psia (a pressure above the equilibrium pressure of the hydride) while being maintained at room temperature (hydriding). After such pressurization has been maintained for approximately one-half an hour, the reactor is purged with helium and again while the purge is in progress is heated to 400° C. and then cooled (dehydriding). These hydriding and dehydriding cycles are repeated until the desired particle size is attained, which usually requires three to four cycles. The catalyst bed is then ready for the production reaction.

Following the last activation cycle, the reactor is heated to 200° C. and pressurized with hydrogen to 100 atmospheres. The feed composition of carbon dioxide and hydrogen is then introduced into the reactor and the product drawn off on a continuous basis at a flow rate determined by a space velocity (ratio of feed rate to total weight of catalyst) not to exceed 1,000 cubic meters (at standard temperature and pressure) per hour per ton of catalyst. A variety of feed compositions may be employed but should not exceed a molar ratio of carbon dioxide to hydrogen of 1 to 10 if continuous activation of the catalyst is desired. Feed compositions with greater amounts of carbon dioxide may tend to smother the catalyst, thereby interfering with the diffusion characteristics of the hydrogen within the alloy. This is therefore the preferred ratio for the production of methane and ethane.

Higher carbon dioxide to hydrogen ratios favor higher ratios of ethane in the final product, as well as the production of methanol and ethanol, particularly at lower reaction temperatures (less than 200° C.). Where these products are desired in the exit stream, alternating cycles of greater hydrogen content (hydrogen ratios of 10 to 1 and above) can be employed to reactivate the catalyst.

Higher space velocities and corresponding feed rates are also possible, but may give lower yields. Nevertheless, faster throughput and lower yields may be more economical depending on the parameters of downstream separation and recycle equipment. A further restriction on the process is the same as that found in conventional methane production techniques, namely, an upper temperature limit is defined for a given pressure where exceeding that limit would result in carbon deposition on the catalyst, either from cracking of the methane or dissociation of the carbon dioxide feed. Carbon deposition is an irreversible phenomenon and should be carefully avoided in all instances. A full discussion of those upper limits is found in an article entitled "Catalytic Methanation" by G. A. Mills and F. W. Steffgen in *Catalysis Reviews*, Vol. 8 at pages 155 to 210, 1974.

The relative proportion of ethane to methane from the foregoing embodiment would be in the range of one part ethane for approximately 20 parts of methane. The relative proportion of ethane in the product mixture can be substantially increased by lowering the temperature of 100° C. This would give a ratio of ethane to methane of approximately one to 10. It is also to be understood that greater yield ratios of ethane to methane and faster reaction rates are attainable under most process conditions by substituting carbon monoxide for carbon dioxide or using a mixture of both of said carbon oxides in the feed stream. Carbon dioxide was employed in the preferred embodiment above for the reason that commercial production rates using this gas as the predominant carbon oxide component in the feed have not been heretofore attainable.

Significant amounts of the corresponding alcohols can also be produced by increasing the molar ratio of carbon oxides to hydrogen in the feed to greater than 1 to 10 and by employing lower process temperatures of around 200° C. or less. Although lower temperatures would produce a less efficient reaction, the value of the product gas may be correspondingly increased by the increased percentage of alcohols and higher hydrocarbons present.

The product stream leaving the catalyst bed will contain the carbon oxide and hydrogen reactants and the products methane and ethane, with an ethane to methane ratio of usually less than 0.1 where the dioxide is the principal component in the feed. Greater ratios of ethane to methane and the presence of methanol, ethanol and liquid hydrocarbons may be enhanced by the feed composition and process conditions selected as discussed above. Each of these products can be separated from the exit stream in conventional fashion if desired and the reactants recycled to the reactor vessel. If the product is going to be used as a fuel, such as a substitute for natural gas, both the hydrogen and the alcohols can be left in the product stream. Whether to leave any or all of these in a fuel stream will of course be determined by the economics of separation and the use to be made of the products. It may be desirable to separate the carbon oxides only and this could be done by conventional adsorption techniques, such as contacting the exit stream with an alkaline solution. If separation of the exit stream into all of its constituents is desired, conventional liquefaction techniques followed by fractionation can be employed for that purpose.

Although but a single embodiment of the present invention has been described, other embodiments and variations will occur to those skilled in the art.

For example, it is possible to combine the titanium and iron intermetallic compounds with known catalytically active metals for this reaction such as ruthenium and nickel, either in the form of mixtures or multi-component (e.g. ternary, quarternary or higher) alloys, or to support those compounds on an inert carrier material or other substrate.

It is also possible, of course, to use various features of the specific embodiment described, such as the catalyst at other temperatures and pressures, and such are within the contemplation of the present invention. Furthermore, many changes of the process steps are possible and are intended to be within the scope of this disclosure. It is therefore to be understood that the foregoing specification merely illustrates and describes a preferred embodiment of the invention and that other embodiments are contemplated within the scope of the appended claims. For example, activation of the catalyst can be achieved, although at a slower rate, by exposure to the hydrogen in the feed stream itself.

I claim:

1. A method of making methane and ethane which comprises contacting hydrogen and at least one oxide of carbon in synthesis proportions at synthesis conditions with a catalyst prepared by alloying titanium and iron in a mole ratio of total titanium to total iron of greater than 0.5 but not more than 3.0 and then exposing such titanium iron alloy to hydrogen at hydriding conditions, the proportions of titanium and iron and the alloying conditions being such as to produce an alloy comprised of an iron titanium bimetallic compound effective to catalyze conversion of hydrogen and oxides of carbon to methane, and said hydriding conditions being such as to hydride at least a portion of said alloy.

2. A method of making methane and ethane according to claim 1 wherein said bimetallic compound has a mole ratio of titanium to iron of at least 1.0.

3. A method of making methane and ethane according to claim 2 wherein said hydriding conditions include exposing said alloy to hydrogen at an elevated temperature and pressure effective to remove oxides from exposed surfaces thereof.

4. A method of making methane and ethane according to claim 3 wherein said hydriding conditions include exposing said alloy to hydrogen at a pressure at least equal to the equilibrium dissociation pressure of iron titanium hydride at the prevailing temperature of the alloy.

5. A method of making methane and ethane according to claim 2 wherein the mole ratio of total titanium to total iron in said alloy is greater than 1.0.

6. A method of making methane and ethane according to claim 5 wherein said synthesis conditions include a catalyst temperature of at least 100° C.

7. A method of making methane and ethane according to claim 6 wherein said synthesis conditions include contacting the catalyst with a gaseous mixture of the reactants at a total pressure of at least 30 atmospheres.

8. A method of making methane and ethane according to claim 2 wherein preparation of the catalyst includes exposing granules of said alloy to hydrogen at a pressure at least equal to the equilibrium dissociation pressure of iron titanium hydride at the prevailing temperature of the granules to hydride the alloy.

9. A method of making methane and ethane according to claim 8 wherein said catalyst preparation includes outgassing said hydrided granules at conditions effective to dehydride the alloy and break said granules into smaller particles.

10. A method of making methane and ethane according to claim 9 wherein the mole ratio of total titanium to total iron in said alloy is at least 1.1.

11. A method of making methane and ethane according to claim 10 wherein said hydriding conditions are such that substantially all of said alloy is converted to its hydride form.

12. A method of making methane according to claim 11 wherein said hydriding conditions include a first step of exposing said granules to gaseous hydrogen at an elevated temperature and pressure effective to remove oxides from exposed alloy surfaces.

13. A method of making methane and ethane according to claim 2 wherein the oxide of carbon is carbon monoxide.

14. A method of making methane according to claim 2 wherein the oxide of carbon is carbon dioxide.

15. A method of making methane according to claim 2 wherein the catalyst is contacted with reactants comprised of hydrogen and a mixture of carbon monoxide and carbon dioxide.

* * * * *